(12) United States Patent
Maluf

(10) Patent No.: US 7,873,181 B1
(45) Date of Patent: Jan. 18, 2011

(54) VISUAL IMAGE SENSOR ORGAN REPLACEMENT: IMPLEMENTATION

(75) Inventor: A. David Maluf, Mountain View, CA (US)

(73) Assignee: The United States of America as represented by the Administrator of the National Aeronautics and Space Administration, Washington, DC (US)

(*) Notice: Subject to any disclaimer, the term of this patent is extended or adjusted under 35 U.S.C. 154(b) by 969 days.

(21) Appl. No.: 11/525,600

(22) Filed: Sep. 21, 2006

Related U.S. Application Data

(63) Continuation-in-part of application No. 11/239,450, filed on Sep. 23, 2005.

(51) Int. Cl.
*G09K 9/00* (2006.01)
*G06K 9/36* (2006.01)
(52) U.S. Cl. .................................. 382/100; 382/276
(58) Field of Classification Search .......... 382/100, 382/276; 381/18
See application file for complete search history.

(56) References Cited

U.S. PATENT DOCUMENTS

| | | | | |
|---|---|---|---|---|
| 5,123,052 | A * | 6/1992 | Brisson | 381/77 |
| 5,795,287 | A * | 8/1998 | Ball et al. | 600/25 |
| 5,999,661 | A * | 12/1999 | Oster et al. | 382/276 |
| 6,681,018 | B1 * | 1/2004 | Asakura et al. | 381/18 |
| 7,280,689 | B2 * | 10/2007 | Bilobrov et al. | 382/166 |
| 7,382,888 | B2 * | 6/2008 | Aylward et al. | 381/97 |
| 2004/0013272 | A1 * | 1/2004 | Reams | 381/1 |
| 2004/0122323 | A1 * | 6/2004 | Vortman et al. | 600/459 |
| 2004/0256561 | A1 * | 12/2004 | Beuhler et al. | 250/339.05 |
| 2005/0137860 | A1 * | 6/2005 | Nam | 704/205 |

FOREIGN PATENT DOCUMENTS

JP 2002-328702 * 11/2002

OTHER PUBLICATIONS

Peter et al. ("An Experimental System for Auditory Image Representations", IEEE transaction on biomedical engineering, vol. 39, No. 2, Feb. 1992).*
Grantham, Spatial Hearing and Related Phenomena, Hearing, Handbook of Perception and Cognitiion 2nd Edition, 1995, 297-345, Academic Press, USA.
Mansur, et al., Sound Graphs: A Numerical Data Analysis Method for the Blind, Journal of Medical Systems, 1985, 163-174, 9-3, Plenum Publishing Corporatiion.

(Continued)

*Primary Examiner*—Vu Le
*Assistant Examiner*—Amara Abdi
(74) *Attorney, Agent, or Firm*—John F. Schipper; Robert M. Padilla

(57) ABSTRACT

Method and system for enhancing or extending visual representation of a selected region of a visual image, where visual representation is interfered with or distorted, by supplementing a visual signal with at least one audio signal having one or more audio signal parameters that represent one or more visual image parameters, such as vertical and/or horizontal location of the region; region brightness; dominant wavelength range of the region; change in a parameter value that characterizes the visual image, with respect to a reference parameter value; and time rate of change in a parameter value that characterizes the visual image. Region dimensions can be changed to emphasize change with time of a visual image parameter.

33 Claims, 9 Drawing Sheets

OTHER PUBLICATIONS

Meijer, An Experimental system for Auditory Image Representations, IEEE Transactions on Biomedical Engineering, Feb. 1992, 112-121, 39-2, IEEE.

Palmer, Neural Signal Processing, Hearing, Handbook of Perception and Cognition 2nd Edition, 1995, 75-121, Academic Press, USA.

Stern, et al., Models of Binaural Interaction, Hearing, Handbook of Perception and Cognitiion 2nd Edition, 1995, 347-385, Academic Press, USA.

Yates, Cochlear Structure and Function, Hearing, Handbook of Perception and Cognitiion 2nd Edition, 1995, 41-73, Academic Press, USA.

* cited by examiner

VISUAL IMAGE SENSOR ORGAN REPLACEMENT: IMPLEMENTATION

RELATED APPLICATION

This application is a continuation-in-part of a patent application entitled "Visual Image Sensor Organ Replacement," U.S. Ser. No. 11/239,450, filed 23 Sep. 2005.

ORIGIN OF THE INVENTION

This invention was made, in part, by one or more employees of the U.S. government. The U.S. government has the right to make, use and/or sell the invention described herein without payment of compensation, including but not limited to payment of royalties.

FIELD OF THE INVENTION

This invention relates to implementation of use of audio signal parameters as representatives of time varying or constant visual signal parameter values.

BACKGROUND OF THE INVENTION

Present development of fast, cheap and miniaturized electronics and sensory devices opens new pathways for the development of sophisticated equipment to overcome limitations of the human senses. Humans rely heavily on vision to sense the environment in order to achieve a wide variety of goals. However, visual sensing is generally available only for a limited visible range of wavelengths, roughly 400 nm (nanometers) to 720 nm, which is a small fraction of the range of wavelengths (180 nm through about 10,000 nm) at which interesting physical effects and/or chemical effects occur. Audible sensing, over an estimated audible range of 200 Hz (Hertz)-20,000 Hz, is similarly limited, but this range is a larger fraction of the audibly interesting range 10 Hz-$10^5$ Hz). Further, use of binaural hearing to provide audible clues as to depth and relative location is generally better developed than are the corresponding mechanisms associated with formation of visible images.

Since the time of Aristotle (384-322 BC), humans have been interested in perceiving what is beyond normal "vision". Roentgen's discovery of X-Rays enabled him to see inside living tissue, and "vision" was thereby extended beyond the naked eye. In the following years, imaging and sensing techniques have developed so rapidly that astronomy, medicine and geology are just few of the areas where sensing beyond the normal visual spectrum has been found useful. Altering and extending human "vision" changes our perception of the world According to some recent research in evolution of the sight system for animals, reported in "What Birds See" by Timothy H. Goldsmith, Scientific American, July 2006, pp. 68-75, certain bird species have a tetra-chromatic color sensing system, with color bands spanning the near-ultraviolet, violet, green and red wavelengths, in contrast to the tri-chromatic (for primates, humns and some birds) or bi-chromatic (for other animals) color sensing systems that cover only two or three visible wavelength bands. The tetra-chromatic color sensing system of the birds allows more subtle sensing of color differences, much as HD radio claims to allow receipt of radio frequencies between the 0.2 kHz signposts of conventional commercial radio. This extra color sensing subtlety available to some birds is not available, and is not likely to become available, generally to humans and/or primates.

Further, the human audible sensing system is capable of learning to process and interpret extremely complicated and rapidly changing auditory patterns, such as speech or music in a noisy environment. The available effective bandwidth, on the order of 20 kHz, may support a channel capacity of several thousand bits per second. The known capabilities of the human hearing system to learn and understand complicated auditory patterns provide a basic motivation for developing a visual image-to-sound mapping system.

What is needed is a system that converts "visual signals", defined herein as signals with at least one associated wavelength in the ultraviolet, the visible and/or the infrared, to one or more audibly perceptible signals with associated audio parameters that can be recognized and distinguished by the human ear. Preferably, these signals should include an audible indication of change, or change rate with time, of one or more visual image parameters. Preferably, these audio signals should provide monaural and/or binaural signaling that is analogous to depth clues and/or distance clues provided by visually perceptible images. Preferably, the audible signal parameters should have an intuitive connection with the visual signal parameters to which the audible signal parameters correspond.

SUMMARY OF THE INVENTION

These needs are met by the invention, which provides a mapping or association between signals representing a selected region of a received visual image and audibly perceptible signals in which M visual signal parameter values (M=1-8) are mapped one-to-one onto a selected set of distinguishable audible signal parameters. External multi-spectral sensors signals are translated into audible signals targeting the same human visual field.

The visual signal is received and one or more visual signal parameters are measured or otherwise provided, including but not limited to distinction between visual signal wavelengths in the ultraviolet, the visible, the near-infrared and the mid-infrared. The audible signal parameter values provided as output include one or more of: an envelope frequency $f_e$; a time rate of change of the envelope frequency (analogous to "chirping" or to a Doppler effect); a carrier frequency $f_c$; an envelope frequency phase $\phi_e$ at a selected time, $t=t_{ph,e}$; a carrier frequency phase $f_c$ at the selected time, $t=t_{ph,c}$; a baseline function b(t) the defines a baseline curve BB; a time rate of change db/dt of the baseline function; a non-undulatory, but possibly time varying, signal amplitude a(t), measured relative to the baseline curve BB; and a time interval (duration) $\Delta t$ for the signal. The human ear may be able to distinguish the phase difference, $\Delta\phi=\phi_e-\phi_c$, but need not recognize the absolute phases, $\phi_e$ and/or $\phi_e$.

DESCRIPTION OF BEST MODES OF THE INVENTION

Figure 1:
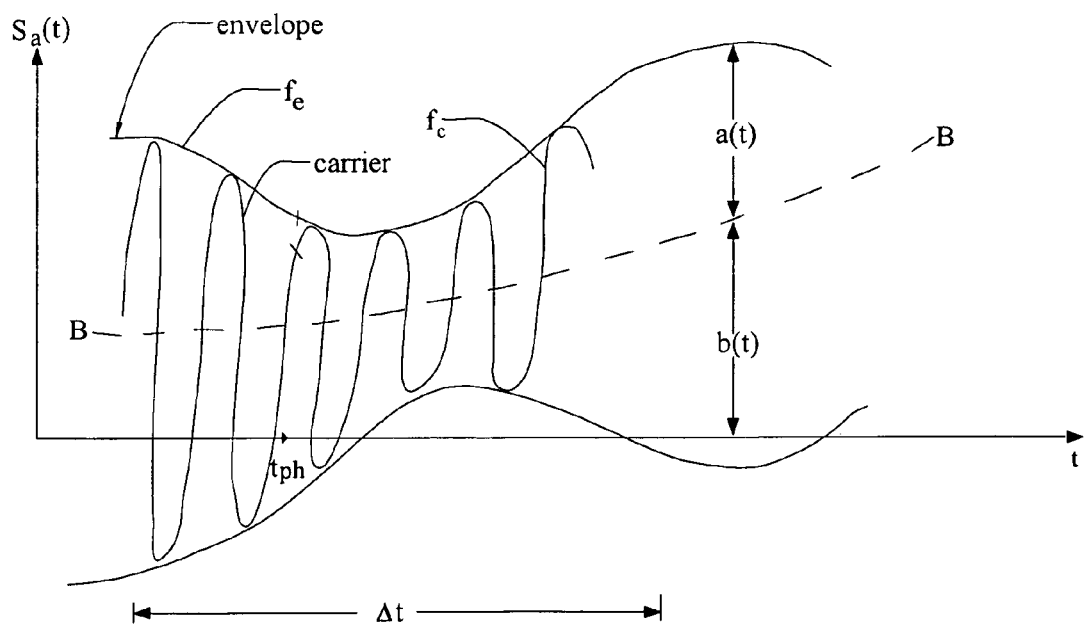
FIG. 1 graphically illustrates several audio signal parameters that can be used in the invention to provide a visual-audio association of parameters.

FIG. 1 graphically illustrates M signal parameter values (M=1-8) that can be used to collectively characterize an undulating, audibly perceptible signal $s_a(t)$ having a single information-bearing (envelope) frequency and a single carrier frequency. This signal can be characterized by: an envelope frequency $f_e$ and corresponding time rate of change of the envelope frequency $df_e/dt$ (analogous to "chirping" or to a Doppler shift); a carrier frequency $f_c$; an envelope frequency phase $\phi_e$ at a selected time, $t=t_{p,eh}$; a carrier frequency phase $f_c$ at the selected time, $t=t_{ph,c}$; a baseline function amplitude b(t), defining a baseline curve BB, and corresponding time rate of change of base line amplitude db/dt; a non-undulatory signal amplitude a(t), measured relative to the baseline curve BB; and a time interval (duration) $\Delta t$ for the signal. The human ear may be able to distinguish the phase difference, $\Delta\phi=\phi_e-\phi_c$, but cannot distinguish the absolute phases, $\phi_e$ and/or $\phi_e$. An audible signal equation incorporating all these features is $$S_a(t)=b(t)+a(t)\cdot\sin\{f_e(t)t+\phi_e\}\cdot\sin\{f_c t+\phi_c\} \quad (1)$$

The maximum number of parameters for the signal shown in FIG. 1 that may be distinguished by the human ear is M=6-8, if the (absolute) selected time, $t=t_{ph}$, and the absolute phases are not included. These M signal parameters may be used to audibly represent a corresponding visual region of an image, such as vertical and horizontal coordinate ranges (versus time) of the visual region (relative to a fixed two-dimensional or three-dimensional system), estimated distance s(t) and/or rate of change of distance ds/dt to a selected center of the region, region brightness, overall region brightness, and region predominant hue (color) or wavelength. Optionally, these audible signal parameters can be presented simultaneously or sequentially, for any corresponding visual image region that is so represented. In a sequential presentation, one or more additional audible signal parameters may be included, if the information corresponding to the additional parameter value(s) is necessary for adequate representation of the image region.

Figure 2:
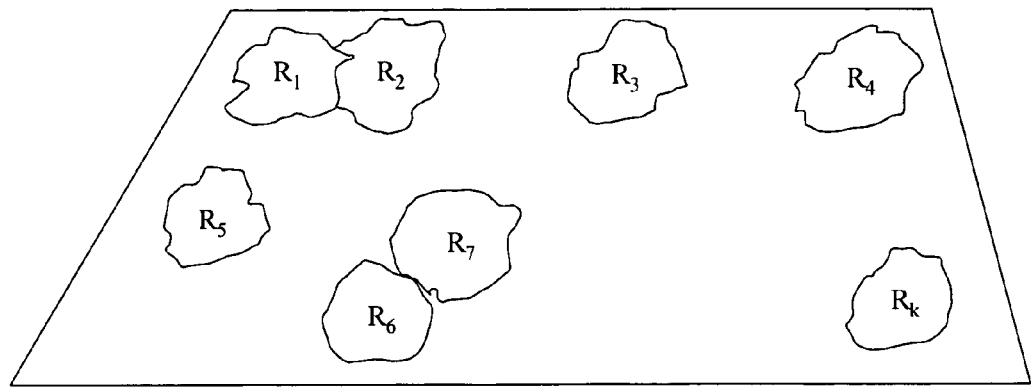
FIG. 2 schematically illustrates (partial) representation of a sequence of regions of a visual image.

The visual image may be decomposed into a sequence of K selected visual image regions $R_k$, (k=1, ..., K, with K≧1; contiguous or non-contiguous; overlapping or nonoverlapping) that make up part or all of the total visual image, for example as illustrated in FIG. 2. The sequence of regions $R_k$, and the corresponding sequence of audible signal parameters, need not exhaust the set of all regions that together make up the visual image. Preferably, the image regions are chosen according to which regions are of most interest. For example, when an image has a single image region (less than the entire image) where one or more image parameters is changing substantially with time, this region may be a primary focus; and if this region slowly changes its location or its physical extent within the total image, the location and breadth of this image region should correspondingly change with time. That is, the horizontal and vertical bounds and/or the center of an image region may move with time within the total image.

If the visual image changes between one time to a subsequent time, the audible parameters representing each selected region $R_k$ may also change with time, in a sequential manner. FIG. 1 graphically illustrates signal parameters corresponding to a mapping that can be implemented to represent a group of visual signal parameters, representing a selected region $R_k$ of the total image, by an audibly perceptible signal or signals.

In one approach, a visual image region $R_k$ is selected and optionally isolated, and the corresponding audibly perceptible signal parameters are presented (1) sequentially within a time interval of selected length (e.g., 5-30 sec) or (2) as part of a single audible signal that incorporates two or more selected audible signal parameter values.

If an audible signal parameter changes with time, continuously or discretely, this change can be presented according to several options: (i) change the audible parameter value continuously at a rate that corresponds to the time rate of change of the corresponding visual parameter value; (ii) change the audible parameter value discretely at a rate corresponding to a discrete time rate of change of the visual parameter value; and (iii) change the audible parameter value discretely, by a selected amount, only when the magnitude of the difference between a first value and a second value of the parameter is at least equal to a threshold magnitude, which will vary with the nature of the visual parameter.

Humans and primates rely heavily on tri-chromatic vision to sense and react to the environment in order to achieve various goals. By contrast, other animals rely heavily, but not exclusively, on smell (e.g., rodents), on sound (e.g., some birds), or on tetra-chromatic vision (other birds). The invention augments or replaces a human sensory visual system, which is deficient in many respects, with one or more auditory signals, in order to achieve the following.

(1) Provide a capacity to sense beyond the human visible light range of the electromagnetic spectrum).

(2) Increase capacity of human sensing resolution, beyond the number of rods and cones in the human eye (approximately 120 million rods and 6 million color sensing cones) that limit the resolution of the images, particularly because humans rely on the subset of cones located in the fovea, which provide humans the highest visual acuity of approximately 1 min of arc resolution within a field of view less than 12 degrees horizontal by 4 degrees vertical in humans.

(3) Provide wider angle equivalent of visual sensory perception, where the shape and location of human eyes limit the effective human field of view to about 200 degrees horizontally by about 150 degrees vertically.

(4) Improve the ability of a human to sense distances, which is presently relatively poor and can be confounded by a wide variety of visual cues.

(5) Allow compensation for movement by the human or changes in the scene; for example, motion smear or blur can make it difficult to resolve images at resolutions achievable when the perspective of an image is not moving or changing.

(6) Allow splitting of user attention (multi-tasking using two or more senses), where a visual image limits the range of other activities that a person can do simultaneously, such as monitoring gauges and reading text concurrently.

(7) Provide audibly perceptible changes in an audible parameter value that correspond to changes, continuous or discrete, in a visual parameter value that are too small or subtle for a human eye to sense or respond to.

(8) Provide an audible parameter value that changes in an audibly perceptible manner only when the corresponding visual parameter changes by at least a threshold amount, and the threshold is selectable according to the environment.

Using the invention, a wide variety of tasks that are difficult or cumbersome to accomplish, using primarily visual indicia, can be met, including the following:

Enabling the user to substantially simultaneously focus attention on multiple aspects of a visual field, or its audible field equivalent;

Embedded human sensing of aircraft performance; and

Audibly indicating micro-fractures and/or thermal distortion in materials.

In order to increase the visual image resolution obtainable via an auditory representation, a mapping is performed to distribute an image in time. Three-dimensional spatial brightness and multi-spectral maps of a sensed image are processed using real-time image processing techniques (e.g., histogram normalization) and are transformed into one or more two-dimensional maps of an audio signal as a function of frequency and of time.

The invention uses a Visual Instrument Sensory Organ Replacement (VISOR) system to augment the human visual system by exploiting the improved capabilities of the human auditory system. The human brain is far superior to most existing computer systems in rapidly extracting relevant information from blurred, noisy, and redundant images. This suggests that the available auditory bandwidth is not yet exploited in an optimal way. Although image processing techniques can manipulate, condense and focus the information (e.g., using Fourier Transforms), keeping the mapping as direct and simple as possible may also reduce the risk of accidentally filtering out important clues. Even a perfect, non-redundant sound representation is subject to loss of relevant information in a non-perfect human hearing system. Also, a complicated, non-redundant visual image-to-audible image mapping may well be more difficult to learn and comprehend than a straightforward visual mapping, while the mapping system would increase in complexity and cost.

Figure 3:
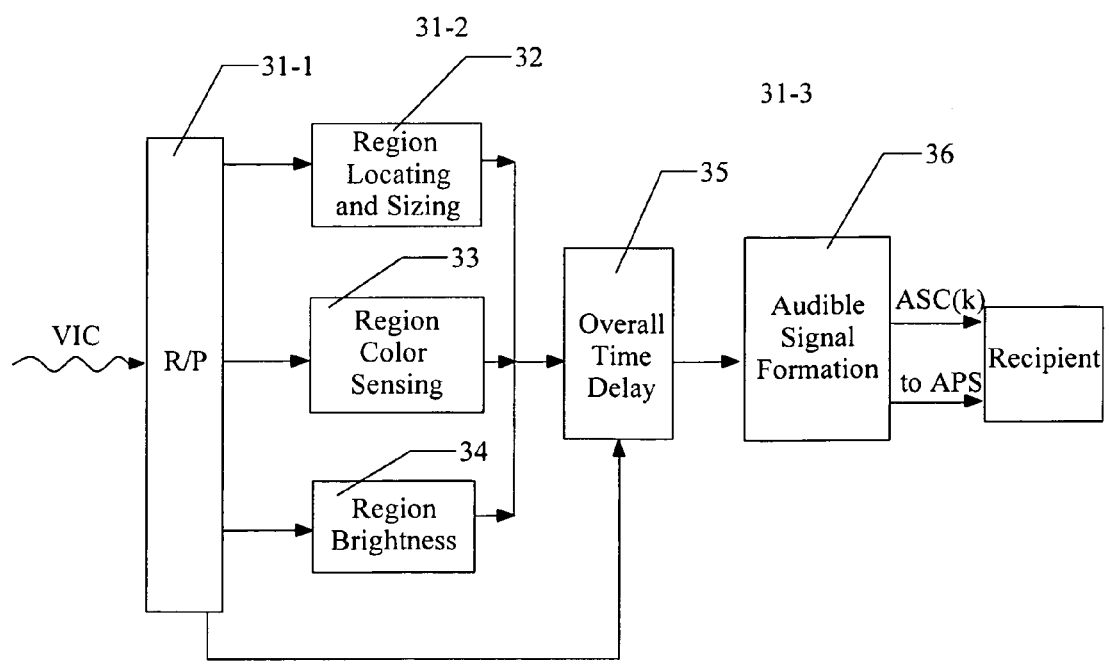
FIG. 3 schematically illustrates a mapping device used to transform visual image region parameters to audibly perceptible signal parameters.

FIG. 3 schematically illustrates a mapping device used to transform selected visual image parameters associated with a region to an audible signal with audibly perceptible parameters. One or more visual image region ("VIR"), representations is received and analyzed by a first stage signal receiver-processor ("R/P") 31-1. The first stage R/P 31-1 analyzes a received VIR and provides one or more (preferably as many as possible) of the following visual signal characterization parameters in a second stage R/P 31-2: vertical and horizontal coordinate ranges of the region and/or its center; optional adjustment in size of region viewed; region predominant hue (color) or wavelength; region average brightness and region peak brightness, using a region locator and sizing mechanism 32, a region predominant (or average) color sensing mechanism 33 and a region brightness sensing mechanism 34. Output signals from the locator mechanism 32, from the color mechanism 33 and from the brightness mechanism 34 are received by a third stage R/P 31-3, which provides a collection of audible signal parameters, including time rate of change TRC of at least one parameter value.

As an example: the predominant or average color output signal from the region color sensing mechanism 33 can be used to determine the envelope frequency $f_e$; the region brightness output signal from the region brightness mechanism 34 can be used to determine the envelope relative amplitude, $a_0$ (constant) or $a(t)$; the vertical and horizontal location output signals from the locator mechanism 32 can be used to determine time duration $\Delta t$ (if the visual image region locations are indexed by a one-dimensional index), or to determine time duration $\Delta t$, envelope frequency $f_e$ (if the visual image region locations are indexed using a two-dimensional index) or change rate, db/dt or $df_e/dt$. The four visual signal parameters can be assigned to four of six audibly perceptible signal parameters (FIG. 1) in $\binom{6}{4}=(6 \cdot 5 \cdot 4 \cdot 3)/(4 \cdot 3 \cdot 2 \cdot 1)=15$ distinguishable ways. More generally, N visual signal parameters can be assigned to M ($\geq$N) audibly perceptible signal parameters in $\binom{M}{N}$ distinguishable ways.

Where the time rate of change option (i) is used for a visual signal parameter value r, one can form an approximating second degree polynomial $$r(t;\text{app}) = \{r(t_p)\{(t-t_{p+1})(t-t_{p+2})(t_{p+2}-t_{p+1})+r(t_{p+1})\{(t-t_p)(t-t_{p+2})(t_{p+2}-t_p)+r(t_{p+2})\{(t-t_p)(t-t_{p+1})(t_{p+1}-t_p)\}\}/\Pi(t_p;t_{p+1};t_{p+2}), \quad (2)$$

$$\Pi(t_p;t_{p+1};t_{p+2}) = (t_{p+2}-t_{p+1})(t_{p+1}-t_p)(t_{p+2}-t_p), \quad (3)$$

$(t_1 < t_2 < \ldots < t_p < t_{p+1} < t_{p+2} < \ldots)$ and compute r(t) and dr/dt using the approximating polynomial r(t; app) and dr(t; app)/dt, respectively. Approximating polynomials of degree higher than two can also be used here.

Where the time rate of change option (ii) is used for a visual signal parameter value r, a sequence of ratios $$v2(t_p;t_{p+1}) = \{r(t_{p+1})-r(t_p)\}/(t_{p+1}-t_p), \quad (4)$$

is computed for the sequence of times $\{t_p\}$.

Where the time rate of change option (iii) is used for a visual signal parameter value r, the time rate of change ratios of interest become $$v3(t_p; t_{p+P}) = 0 \ (\text{if}|r(t_p) - r(t_{p+q})| < \Delta r(thr) \ \text{for } q = 1, 2, \ldots, P-p) \quad (5)$$

$$= \{r(t_{p+P}) - r(t_p)\} / (t_{p+P} - t_p)(\text{if}|r(t_p) - r(t_{p+q})| \geq \Delta r(thr)$$

$$\text{for } q = 1, 2, \ldots, P-p-1 \text{ and } |r(t_p) - r(t_{p+P})| \geq \Delta r(thr).$$

The analysis performed by each of the mechanisms 32, 33 and 34 is not instantaneous, and the associated time delays may not be the same for each analyzer. For this reason, an overall time delay $$\Delta t(o1) \geq \min\{\Delta t(\text{location,size}), \Delta t(\text{color}), \Delta t(\text{brightness})\} \quad (6)$$

is preferably imposed, using a time delay mechanism 35, before an audible signal (or audible signal sequence) incorporating the 1 through M=M1+M2 audible signal parameters is audibly displayed, where M2 is the number of parameter values that can change with time and M1 is the number of remaining parameters. If the audible signal parameters are displayed sequentially, mot simultaneously or collectively, this time delay might be reduced or eliminated. The overall time delay is implemented by a time delay mechanism 35, which incorporates an appropriate time delay value for each of the audible signal parameters received from the first stage R/P 31-1. An audible signal formation mechanism 36 (optional) forms and issues either: (1) an audibly perceptible, ordered sequence of the set of M audible signal components ASC(m), m=1, ..., M, (or a subset thereof), or (2) a collective audibly perceptible signal APS incorporating the set (or a subset) of the audible signal components. The output signal from the audible signal formation mechanism 36 is perceived by a human or other animal recipient.

Figure 4:
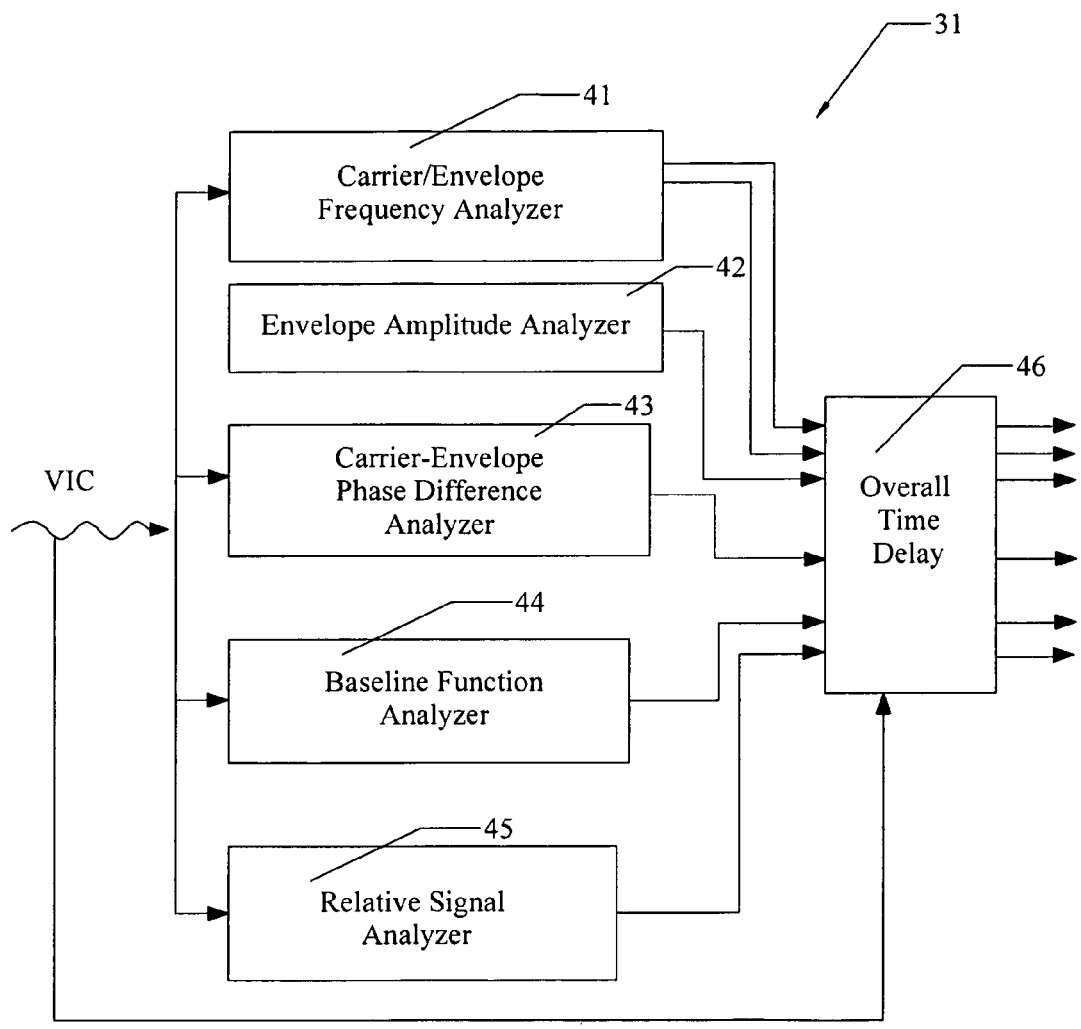
FIG. 4 illustrates a suitable receiver/processor used in FIG. 3.

The R/P 40, illustrated in FIG. 4, includes one or more of the following; a carrier/envelope frequency ($f_c$) analyzer 41; an envelope amplitude analyzer 42; an envelope-carrier frequency phase difference ($\Delta\phi$) analyzer 43 and baseline function (b(t)) analyzer 44 that estimate the phase difference at a selected time and determines the baseline function and baseline time rate of change; and a relative signal amplitude ($a_0$ or a(t)) analyzer 45, relative to the baseline function at a corresponding time.

The analysis performed by each of these analyzers is not instantaneous, and the associated time delays may not be the same for each analyzer. For this reason, an overall time delay $$\Delta t(o2) \geq \min\{\Delta t(f_c), \Delta t(f_e), \Delta t(\Delta\phi), \Delta t(b), \Delta t(a)\} \quad (7)$$

is preferably imposed before an audible signal incorporating the M converted visual signal parameters is audibly displayed. If the converted visual signal parameters are audibly displayed sequentially, rather than simultaneously, this time delay might be reduced or eliminated. The overall time delay is implemented by a time delay mechanism 46, which incorporates an appropriate time delay for each of the audible parameters received from the R/P 31. A signal formation module 47 forms a composite audible signal representing an audible image component, and issues this component as an output signal.

Where the amplitude a(f) is constant, the signal shown in FIG. 1 may be represented in an alternative form $$F_{VIR} = b(t) + a_0 \sin\{f_e(t - t_\phi) + \Delta\phi\} \sin\{f_e(t - t_\phi)\} \quad (8)$$
$$= b(t) + a_0\{\cos\{(f_c - f_e)(t - t_\phi) - \Delta\phi\} - a_0\{\cos\{(f_c + f_e)(t - t_\phi) + \Delta\phi\}$$

The carrier/envelope frequency analyzer 42 forms a sequence of correlation signals, computed over a time interval of length T, $$C1(f_{cs}) = (1/T)\int F_{VIR}(t) \sin\{f_{cs}t\} dt, \quad (9A)$$

$$C2(f_{cs}) = (1/T)\int F_{VIR}(t) \cos\{f_{cs}t\} dt, \quad (9B)$$

at each of a spaced apart sequence of "translated" carrier frequencies, $f_{c1}$ in a selected carrier frequency range, $f_{c1} \leq f_{cs} \leq f_{c2}$, where $f_{cs}$ is not yet known, and provides an estimate of two spaced apart frequencies $f_{cs1} = f_c + f_e$ and $f_{cs2} = f_c - f_e$, associated with the VIR, where the correlation combination, $C1^2 + C2^2$, has the highest magnitudes. The envelope and carrier frequencies are then estimated from $$f_c = (f_{cs1} + f_{cs2})/2, \quad (10A)$$

$$f_e = (f_{cs1} - f_{cs2})/2. \quad (10B)$$

The envelope-carrier phase difference $\Delta\phi$ and relative amplitude $a_0$ are determined by computing the correlations $$(1/T)\int F_{VIR}(t) \sin\{f_e(t-t_\phi)\} dt = a_0 \cos \Delta\phi, \quad (11A)$$

$$(1/T)\int F_{VIR}(t) \cos\{f_e(t-t_\phi)\} dt = a_0 \sin \Delta\phi, \quad (11B)$$

from which the quantities $a_0$ ($\geq 0$) and $\Delta\phi$ are easily determined. The baseline function b(t) is then determined from $$b(t) = F_{VIR}(t) - a_0\{\cos\{(f_c - f_e)(t - t_\phi) - \Delta\phi\} - a_0\{\cos\{(f_c + f_e)(t - t_\phi) + \Delta\phi\}. \quad (12)$$

The frequency difference ($f_c - f_e$) and frequency sum ($f_c + f_e$) values are distinguished from each other in a normally functioning human auditory system if the sum-frequency difference is at least equal to a threshold value, such as 250 Hz.

Figure 5:
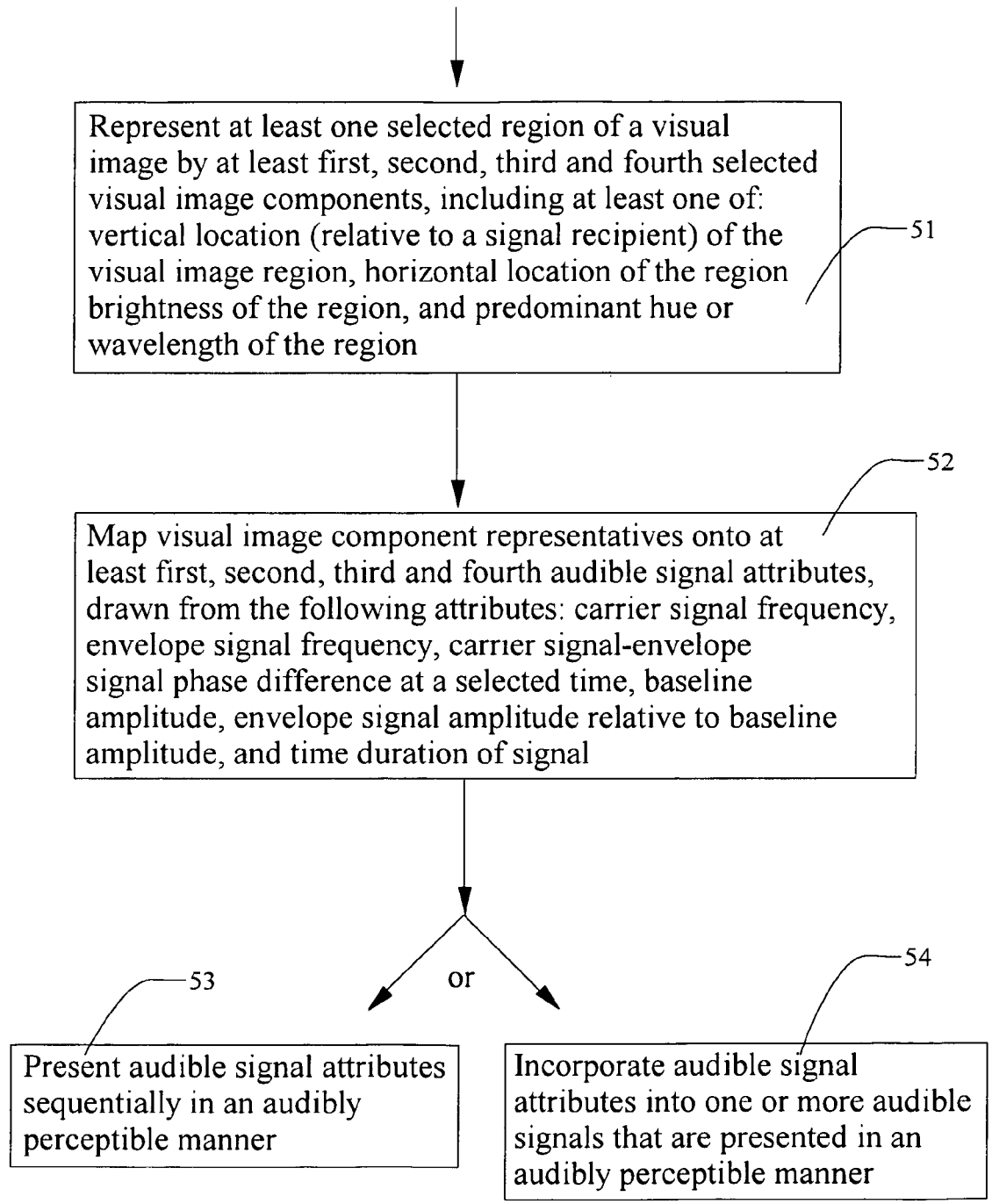
FIG. 5 is a flow chart illustrating practice of an embodiment of the invention.

FIG. 5 is a flow chart illustrating a method for practicing the invention. In step 51, at least one selected region of a visual image is represented by N selected visual image parameters, including at least one of: vertical and horizontal location coordinates and time rate of change of location coordinate(s), relative to a signal recipient, of the region; region predominant hue or wavelength, region brightness (average and/or peak); and time rate of change of a visual signal parameter. In step 52, the visual image region representatives are mapped onto M audible signal attributes (M$\geq$N), drawn from the following set of attributes: carrier signal frequency; envelope signal frequency and time rate of change of envelope frequency; carrier signal-envelope signal phase difference at a selected time; baseline amplitude and time rate of change of baseline amplitude; envelope signal amplitude relative to baseline amplitude; and signal time duration. In step 53, the audible signal attributes are presented sequentially in an audibly perceptible manner to the recipient. In an alternative step 53 (step 54), the audible signal attributes are received and incorporated in one or more audible signals that is/are presented in an audibly perceptible manner to a recipient.

The invention can be applied to provide audibly perceptible and distinguishable signals, representing one or more selected regions of a visually perceptible image, for a sight-impaired person. Where more than one VIR is represented, the audible signal representatives of the VIRs are preferably presented sequentially, with a small separation time interval (as little as a few tens of msec) between consecutive representatives.

Where the visual image is a line drawing or other binary representation, the audible signal components can be configured to represent curvilinear and linear shapes, sizes and intersections. Where the visual image primarily represents interaction of dominant color masses in different regions of the image, the dominant hues and shapes of these interacting regions can be represented audibly. For other reasons, a non-sight-impaired person may prefer to focus attention on attributes of a region of an image that can be represented more accurately or intuitively by non-visual signals, for example, to extend the (visual) wavelength range of signals that can be perceived.

The invention can be applied to "enrich" image detail or manifest more clearly some image details that are not evident where the region is viewed solely with reference to visible light wavelengths. For example, some details of a region may be hidden or muddled when viewed in visible wavelength light but may become clear when the region is illuminated with, or viewed by, an instrument that is sensitive to, near-infrared light (wavelength $\lambda \approx 0.7$-$2$ μm) or mid-infrared light ($\lambda \approx 1$-$20$ μm) or ultraviolet light ($\lambda \leq 0.4$ μm). These hidden details can be converted to audible signal parameter values that are more easily audibly perceived as part of a received signal. Operated in this manner, the invention can separately compensate for a relatively narrow (or relatively broad) visible wavelength sensitivity of the viewer and a relatively narrow (or relatively broad) auditory frequency sensitivity of the same viewer or of a different viewer-recipient. Operated in this manner, the visible wavelength sensitivity of a first (visual image) viewer of the image region can be adjusted and compensated for electronically by adjusting the audible wavelength range of one or more of the audible signal parameters, before the transformed audible signal is received by the same viewer or by a different viewer.

The invention can also be applied to provide audible signal components representing shape signatures, sizes and estimated separation distances for objects that cannot be seen, or that are seen very imperfectly, because of signal interference, signal distortion and/or signal attenuation by the ambient environment. This may occur in a hazardous environment where fluids present provide an opaque, darkened or translucent view of objects in the environment, including moving or motionless persons and objects that present a hazard This interference may also occur in an airborne environment in which rain, snow, hail, sleet, fog, condensation and/or other environmental attributes prevent reasonably accurate visual perception of middle distance and far distance objects. A visual image region that is likely to experience interference can be converted and presented as a sequence of audio signal attributes that can be more easily or more accurately perceived or interpreted by an operator of an aircraft (airborne or on the ground). The audio signal attributes may be extended to include estimated closing velocity between the operator/aircraft and the not-yet-seen object.

The invention can also be applied, in an environment of visual "confusion," to focus on and provide information only on important details among a clutter of unimportant details. The important details may be characterized by certain parameters, and the system may focus on initially-visual details that possess one or more of these parameters, converting the relevant information to audibly perceptible signals that contain this (converted) information. An example is a specified aircraft approaching a destination airport surrounded by other airborne aircraft: the specified aircraft may wish to focus on and receive relevant (converted) audibly perceptible information for the immediately preceding aircraft and the immediately following aircraft in a queue formed by an air traffic controller to provide an orderly sequence of touchdowns at the destination airport.

The invention can also be applied where visual signals representing the image are more likely to experience signal interference, signal distortion, signal attenuation and/or similar signal impairments than are selected corresponding audible signals that represent certain parameters in these visual signals. The visual signals (now converted to audible signals) may be transmitted through the ambient environment with reduced signal interference, reduced signal distortion and/or reduced signal attenuation, and may be interpreted more accurately by a signal recipient.

The invention can also be applied to provide an audible signal representing P dimensions (P>2), formed or converted from a two-dimensional visual image region. The audible signal may, for example, provide depth clues, clues about a dominant hue or color or brightness, if any, and clues about the maximum fineness of detail associated with the image region, in addition to normal two-dimensional information.

Consider a visual image region, such as a limited region of the image, and let $p(t)$ represent an image region parameter that changes with time. The parameter may change continuously, or even differentiably, but in other more general situations $p(t)$ may also change by a discrete amount at each of a sequence of spaced apart times $\{t_n\}_n$, as $\{p(t_n)\}_n$, where $p(t_n) \neq p(t_{n+1})$, as discussed in the preceding. Assuming that $p(t_n)+p(t_0) \neq 0$ for $n=1, 2, \ldots$ one can form a normalized parameter $$q(t_n) = \{p(t_n)-p(t_0)\}/\{p(t_n)+p(t_0)\}, \quad (13A)$$

$$p(t_n)/p(t_0) = \{1-q(t_n)\}/\{1+q(t_n)\}, \quad (13B)$$

which represents a difference or a ratio of a subsequent parameter value, relative to an initial or preceding parameter value. This difference or ratio can be represented audibly by a baseline signal amplitude difference $(b(t_n)-b(t_0))$, amplitude ratio $(b(t_n)/b(t_0))$, envelope frequency difference $(f_n-f_0)$, or envelope frequency ratio $(f_n/f_0)$, among other combinations.

Figure 6:
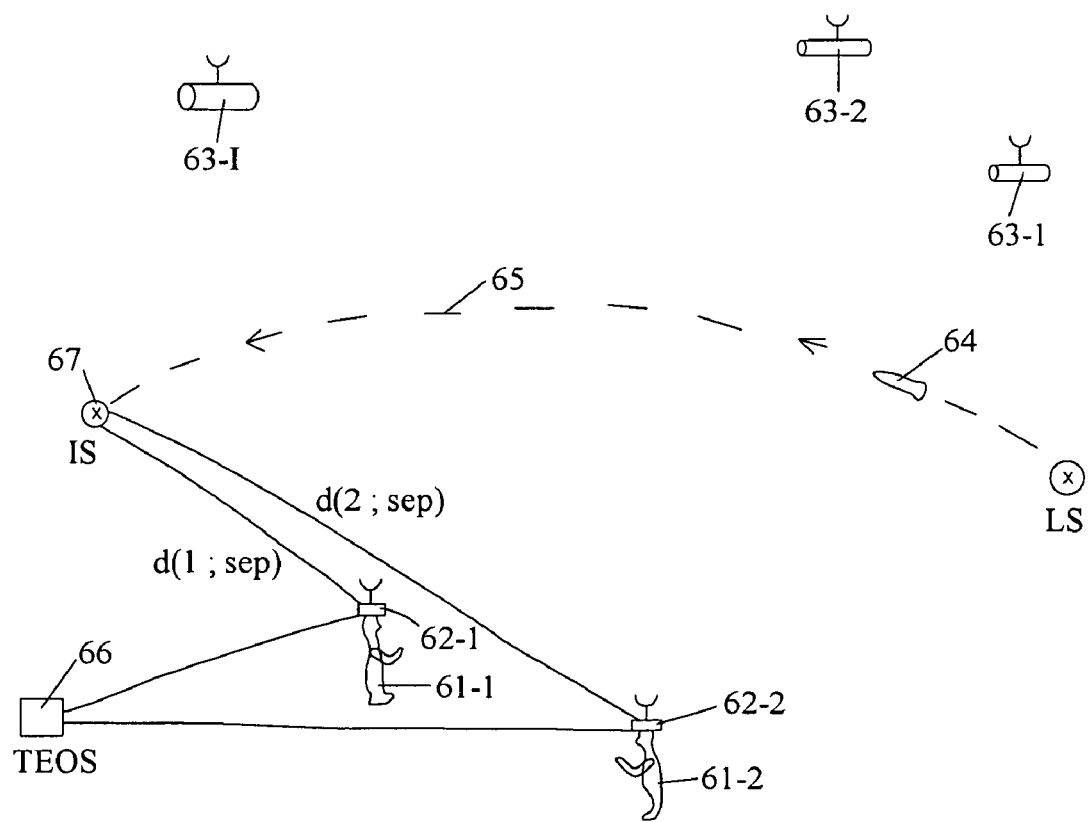
FIG. 6 illustrates an application of the system in a battlefield situation.

As an example of application of the VISOR system, consider a battlefield situation in which one or more combatants, or one or more equipment items, are exposed to artillery shells or other projectiles, as illustrated in FIG. 6 and discussed in more detail in Appendices A, B and C.

In a first version, each combatant wears or carries a location determination ("LD") system, such as GPS, and is aware of the combatant's present location coordinates within an accuracy of a few meters. A simple differential equation for a projectile ballistic trajectory is posited, and two or more observations, spaced apart in time, of the projectile location from each of two observers allows estimation of the relevant shell trajectory parameters, including projectile launch point, projectile impact point and time, and projectile explosive load, from which projectile injury and/or projectile lethality regions can be estimated. Where the combatants are or may be within the disability or injury or lethality region for the projectile, the combatants can be notified collectively of this development by use of an audible (or visual) warning signal, such as a signal with monotonically decreasing (or increasing) frequency, with a final frequency value f(end) that is near to or below a frequency corresponding to disablement or injury or lethality. In this instance, each combatant receives a separate audible (or visual) warning signal with monotonically varying frequency, having a final frequency f(end) that is specific for that combatant's present location on the battlefield. That is, one combatant may be within an injury/lethality region, and another combatant may be outside this region, with a separate audible (or visual) warning signal for each.

Where M ($\geq 3$) observations of projectile location are provided, projectile trajectory accuracy is enhanced by use of a statistically weighted average of trajectory location points. Distinction between trajectories of two or more projectiles that are present at substantially the same time is also available.

In a second version, the audible (or visual) warning signal has an undulatory signal frequency and/or an undulatory signal intensity, which is different for a combatant location inside, as opposed to outside, a probable disability or injury or lethality region relative to the estimated impact site.

In third and fourth versions, at least one (reference) combatant, but less than all the combatants, wears or carries an LD system, and the injury or lethality region is estimated for the reference combatant. When the reference combatant is within the injury or lethality region, an appliance worn by the reference combatant issues an audible (or visual) warning signal that is recognized by all nearby combatants.

Consider a battlefield situation in which one or more combatants, 61-$i$ ($i=1, 2, \ldots$) are exposed to artillery shells or other projectiles, as illustrated in FIG. 6. Each combatant, 61-$i$ wears or carries an appliance 63-$i$ ($i=1, 2, \ldots$), including a receiver-processor for GPS signals and/or other location determination ("LD") signals, received from LD transmitters 65-$j$ ($j=1, \ldots, J; J \geq 2$) that are spaced apart from the combatants. The appliance 65-$i$ associated with each combatant 61-$i$ is aware of the appliance location coordinates (xi, yi, zi) to within an acceptably small inaccuracy. If differential GPS ("DGPS") signals are used, the appliance location can be determined to within an inaccuracy of no more than one meter.

A projectile 62 is launched from a launch site location LS, spaced apart from the combatants 61-$i$, roughly targeting the combatants and following a trajectory 67 that can be visually or (preferably) electromagnetically observed and estimated. For example, a trajectory estimation system disclosed in Appendices A, B and C, or any other system with acceptable promptness of response, can be used for trajectory observation and estimation. A trajectory observation and estimation system 66 observes and provides a prompt, accurate estimation of the projectile trajectory 67, including but not limited to an estimate of the impact site location IS for the projectile 62. The location coordinates ($x_{67}$, $y_{67}$, $z_{67}$) for the projectile impact location 67 are promptly transmitted to each appliance 63-$i$, which promptly computes the separation distance $$d(i;\text{sep}) = \{(xi-x_{67})^2 + (yi-y_{67})^2 + (zi-z_{67})^2\}^{1/2}, \quad (14)$$

and generates an audible, time varying signal $S_a(t; i)$, illustrated graphically in different versions in FIGS. 8A, 8B, 9A and 9B, that is communicated to the associated combatant 61-$i$. Optionally, each combatant 61-I receives a separately determined audible signal $S_a(t; i)$ that is chosen or customized for that combatant's hearing system (including taking account of that combatant's hearing acuity or audible signal sensitivity versus frequency). In one version, the audible signal $S_a(t; i)$ begins at a relatively high, but audible perceptible frequency f(0), and quickly and monotonically decreases to an end frequency f(end) that is monotonically decreasing with decrease of separation distance d(i; sep) for the particular combatant 61-$i$. Optionally, the audible signal $S_a(t; i)$ either terminates at the end frequency f(end) or continues at that end frequency.

Figure 7:
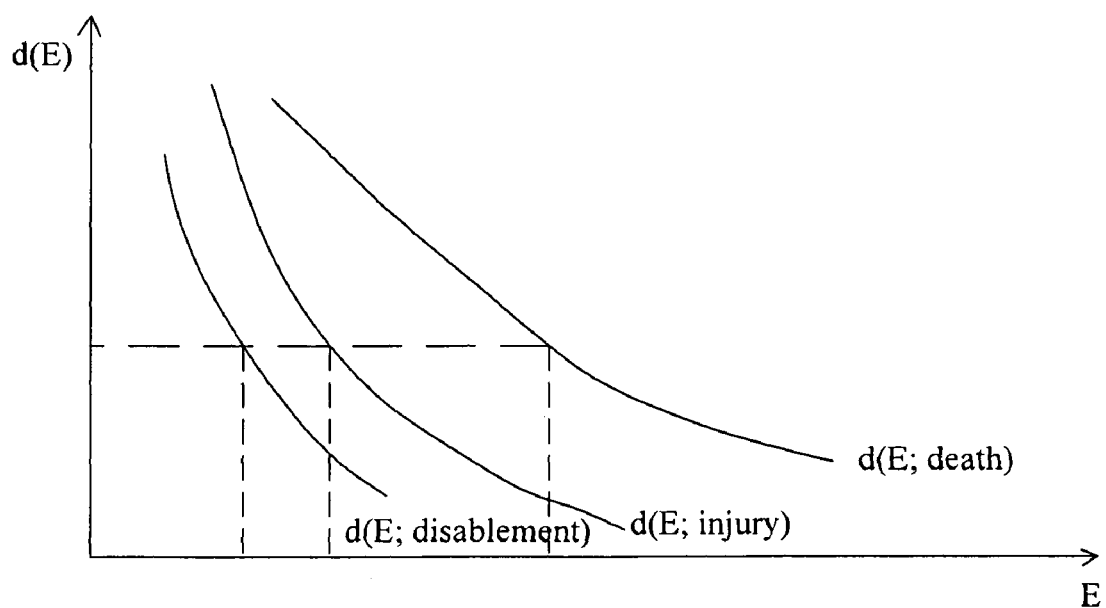
FIG. 7 graphically illustrates variation of estimated projectile impact effective distance d(E), for death or serious injury to a nearby combatant or disablement of an equipment item, as the projectile explosive load E varies.

In a first version, the combatant 61-$i$ or the appliance 63-I compares the end frequency f(end) with a frequency f(caution) (for which the combatant has been trained) to determine if the estimated impact location 67 of the projectile is close enough (within a distance d(E), depending upon the estimated explosive load E, illustrated in FIG. 7) to the combatant's own location to possibly cause death or serious injury to an exposed combatant. If f(end)≦f(caution), the combatant quickly takes defensive maneuvers, such as reducing exposure to the projectile's explosive force. If the estimated impact site location IS is further away and f(end)>f(caution), the combatant may elect to take no defensive maneuvers. Normally, a cautionary distance d(caution) varies inversely with an estimate of the explosive load E carried by the projectile 62.

In a second version, the appliance 63-$i$ numerically compares the estimated separation distance d(i; sep) with d(caution), computed for the estimated explosive load of the projectile 62, and communicates the result of this comparison audibly to the associated combatant 61-$i$, using an audible signal $S_a(t; i)$ with monotonically varying frequency f that decreases to f(end) (to be compared mentally with f(caution)) according to the separation distance d(i; sep).

Alternatively, the audible signal frequency f(t) may increase monotonically as d(i; impact) decreases so that f(end)≧f(caution) causes implementation of defensive maneuvers by the combatant 61-$i$.

In the first version, each combatant 61-$i$ receives a separately determined audible signal $S_a(t; i)$. In the second version, applicable where the relative locations of a group of combatants is substantially unchanging (the combatants remain in place or move as a group), a single audible signal $S_a(t)$ can be provided, keyed to a separation distance d(ref; sep) of the estimated impact location from a reference combatant (real or virtual) for the group. In this version, the frequency range f(end)≦f≦f(0) and the cautionary frequency f(caution) are preferably chosen to take account of the hearing acuities of each member in the group of combatants. Different versions of this example are discussed in detail in Appendices A, B and C.

As another example, consider a visual image region, a portion of a larger image, in which an object of interest moves toward the viewer or away from the viewer at a substantial speed. Because of this movement, the apparent size (diameter viewed transverse to the direction of sight) of the object changes substantially with time. If the visual image is reduced in size and (re)defined so that this object is the dominant feature of the (resulting visual image, change of the diameter with time can be represented as an envelope frequency or baseline amplitude, for example, with envelope frequency or baseline amplitude changing in proportion to the increase (or decrease) with time of the diameter of the object.

The system includes a "focus" mechanism (optional) that permits a visual image region (part of a larger image) to be discretely or continuously reduced or increased or otherwise adjusted in size (horizontally and vertically, independent of each other) to redefine, and focus on, a selected smaller visual image region, in order to more clearly display the image temporal changes that are of most importance. This adjustment in visual image region size can be implemented discretely by drawing an initial quadrilateral or other polygon (rectangle, trapezoid, etc) as a border around the region to which the visual image is restricted. Optionally, the resulting visual image region, thus redefined, maintains its new shape, with an image diameter that increases or decreases according to the change in diameter that occurs as a result of definition of the selected smaller visual image region.

Appendix A

Example of Projectile Trajectory Estimation

Where combatants are present on a battlefield and are exposed to artillery or armored vehicle fire, the injury and fatality count can be reduced if a probable impact point and a probable lethality radius for the shell or other projectile can be quickly estimated and communicated to the combatants. This requires some knowledge of the projectile trajectory, preferably including probable launch point, probable explosive load and probable impact point, as well as knowledge of other flight variables.

The approach provides a procedure for quickly estimating relevant projectile trajectory parameters and communicating this information in a format that allows substantially instantaneous recognition of whether a combatant is inside or outside a probable lethality or injury or disablement region for impact or explosion of the projectile. This information can be communicable to a group of adjacent combatants, to each combatant individually, and/or to users of equipment items on a battlefield.

The approach is part of a system and method for (i) estimating relevant projectile trajectory parameters from two or more temporally spaced projectile observations from each of two or more spaced apart observers, (ii) estimating probable launch point coordinates, impact point coordinates, time of projectile impact and probable injury/lethality/disablement region (for each of two ore more combatants) from these parameters, (iii) use of (optional) subsequent observations of projectile locations to improve the accuracy of impact prediction and to distinguish between trajectories of two or more projectiles that may be present at the same time.

In a first version, each combatant wears or carries a location determination ("LD") system, such as GPS, and is aware of the combatant's present location coordinates within an accuracy of a few meters. A simple differential equation for a projectile ballistic trajectory is posited, and two or more observations, spaced apart in time, of the projectile location from each of two observers allows estimation of the relevant shell trajectory parameters, including projectile launch point, projectile impact point and time, and projectile explosive load, from which projectile injury and/or projectile lethality regions can be estimated. Where the combatants are or may be within the disability or injury or lethality region for the projectile, the combatants can be notified or warned collectively of this development by use of an audible (or visual) warning signal, such as a signal with monotonically decreasing (or increasing) frequency, with a final frequency value f(end) that is near to or below a frequency corresponding to disability or injury or lethality. In this instance, each combatant receives a separate audible (or visual) warning signal with monotonically varying frequency, having a final frequency f(end) that is specific for that combatant's present location on the battlefield. That is, one combatant may be within an injury/lethality region, and another combatant may be outside this region, with a separate audible (or visual) warning signal for each.

Where M ($\geq 3$) observations of projectile location are provided, projectile trajectory accuracy is enhanced by use of a statistically weighted average of trajectory location points. Distinction between trajectories of two or more projectiles that are present at substantially the same time is also available.

In a second version, the audible (or visual) warning signal has an undulatory signal frequency and/or an undulatory signal intensity, which is different for a combatant location inside, as opposed to outside, a probable disability or injury or lethality region relative to the estimated impact site.

In third and fourth versions, at least one (reference) combatant, but less than all the combatants, wears or carries an LD system, and the injury or lethality region is estimated for the reference combatant. When the reference combatant is within the injury or lethality region, an appliance worn by the reference combatant issues an audible (or visual) warning signal that is recognized by all nearby combatants.

FIG. 6 illustrates a general environment, with two or more combatants, 61-$n$ ($n=1, \ldots, N; N \geq 2$), present and exposed to artillery shells or other projectiles 62 that are directed against the combatants. In one embodiment, each combatant 61-$n$ wears or carries a receiver-processor 63-$n$, including an antenna 64-$n$, that receives location determination ("LD") signals from Q spaced apart LD signal sources 65-$q$ ($q=1, \ldots, Q; Q \geq 3$) and estimates the present location coordinates, $r_n=(x_n, y_n, z_n)$ of the combatant 61-$n$ or of the antenna 64-$n$. The receiver/processor 63-$n$ also receives trajectory parameter information ("TPI") from one or more TPI sources 66-$p$ ($p=1, \ldots, P; P \geq 1$) that track and report TPI for one or more visible trajectories 67 corresponding to at least one projectile 62. Determination or estimation of trajectory information from two or more observers at two or more spaced apart observation times is presented in Appendix C.

It is assumed here that the TPI signals for a given trajectory 62 are received by a receiver-processor 63-$n$, including information that permits estimation of at least one of (i) launch site coordinates, $r_L=(x_L, y_L, z_L)$, (ii) impact site coordinates, $r_I=(x_I, y_I, z_I)$, and (iii) probable explosive load E of the projectile. The receiver-processor 63-$n$ computes a separation distance $$d(n; sep)=\{(x_I-x_n)^2+(y_I-y_n)^2+(z_I-z_n)^2\}^{1/2}, \quad \text{(A-1)}$$

and compares this separation distance with a probable impact effect distance, d(E)=d(E; injury or d(E; death), illustrated graphically in FIG. 7.

Figure 8A:
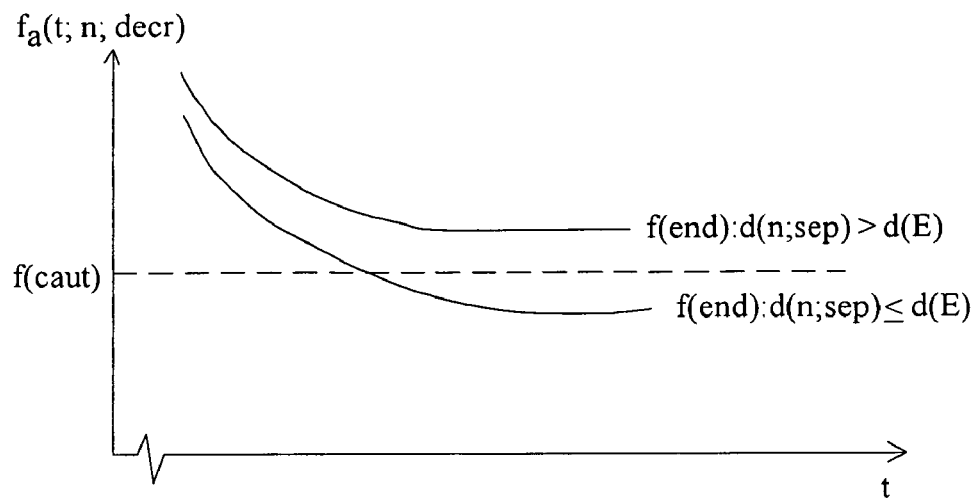
FIGS. 8A, 8B, 9A and 9B graphically illustrate frequencies and intensities of audible signals used in different versions of a projectile impact example.
Figure 8B:
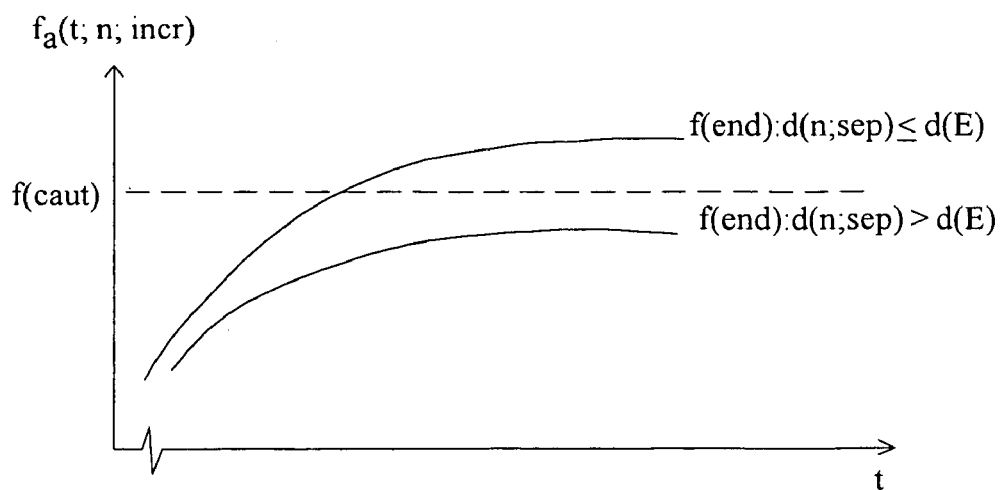

If the Condition $$d(n; sep) \leq d(E) \quad \text{(A-2)}$$

is satisfied so that injury or death from the projectile (which has not yet reached the impact site) is probable, the receiver-processor 63-$n$ generates a first audible (or visual) warning signal $s_a(t; n; 1)$ with a monotonically decreasing frequency, $f=f_i(t; n; decr)$ (FIG. 8A) or monotone increasing, $f=f_i(t; n; incr)$ (FIG. 8B). The distance d(E) may be different in different directions, measured from the estimated impact site, and may be different for each combatant, based on the protective gear worn by each combatant If the signal frequency $f_i(t; n; decr; 1)$ is monotone decreasing (FIG. 8A) and decreases below (preferably substantially below) a known cautionary frequency, f=f(caut), the corresponding combatant 61-$n$ is made aware that he/she is likely to suffer injury or death from explosion or impact of the incoming projectile, and the combatant should quickly seek cover or protection, if possible. If the signal frequency, $f=f_i(t; n; incr; 1)$, is monotone increasing (FIG. 8B) and increases above (preferably substantially above) a known cautionary frequency, f=f(caut), the corresponding combatant 61-$n$ is made aware that he/she is likely to suffer injury or death from explosion or impact of the incoming projectile, and the combatant should seek cover or protection, if possible. If d(n; sep)>d(E) so that injury or death from explosion of the incoming projectile is less likely or unlikely, the audible (or visual) signal frequency, $f=f_i(t; n; decr; 1)$ will stop decreasing at an end frequency, f(end)>f(caut), and the audible (or visual) signal frequency, $f=f_i(t; n; incr)$ will stop increasing at an end frequency, f(end)<f(caut), as illustrated in FIGS. 8A and 8B, respectively.

In this first version, the location of each combatant 61-$n$ is known, to within an inaccuracy of a few meters or less, using an LD device that is part of the receiver-processor 63-$n$, and a separation distance d(n; sep) is calculated for each combatant 61-$n$, preferably using information received at and/or computed by the corresponding receiver-processor 63-$n$. The condition in Eq. (A-2) is tested separately for each combatant 61-$n$ to determine if this condition is satisfied. For each combatant 61-$n$ for which the condition (A-2) is satisfied, the receiver-processor 63-$n$ generates a first audible (or visual) warning signal $s_a(t; n; decr)$ in which the monotone decreasing frequency $f_i(t; n; decr)$ decreases to substantially below the cautionary frequency f(caut); or, alternatively, the monotone increasing frequency $f_i(t; n; incr)$ increases to substantially above the cautionary frequency f(caut). Where the condition (A-2) is not satisfied for a particular combatant 61-$n$, the monotone decreasing frequency $f_i(t; n; decr)$ terminates or plateaus at an end frequency f(end)>f(caut); and the monotone increasing frequency $f_i(t; n; incr)$ terminates or plateaus at an end frequency f(end)<f(caut). Optionally, the cautionary frequency f(caut) can be chosen separately for each combatant, to approximately coincide with a frequency of maximum audible (or visual) sensitivity for that combatant, to compensate for differences in frequency sensitivity between combatants.

Figure 9A:
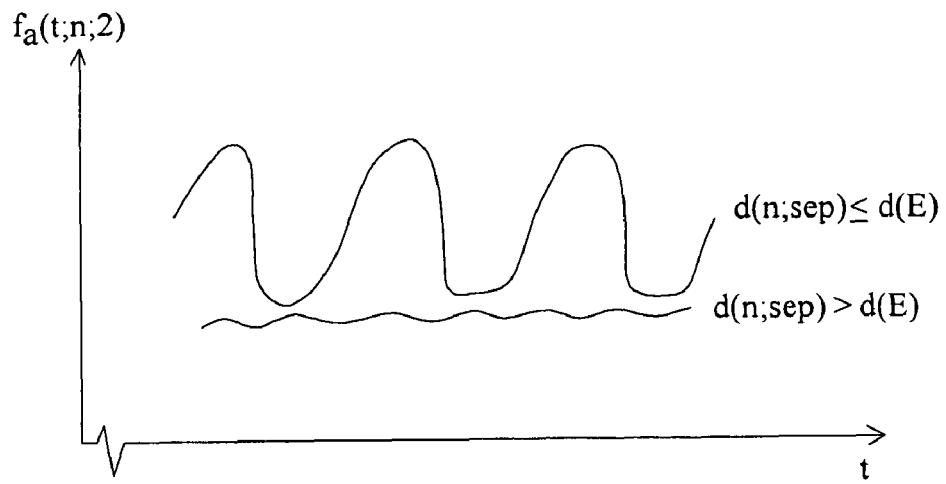
Figure 9B:
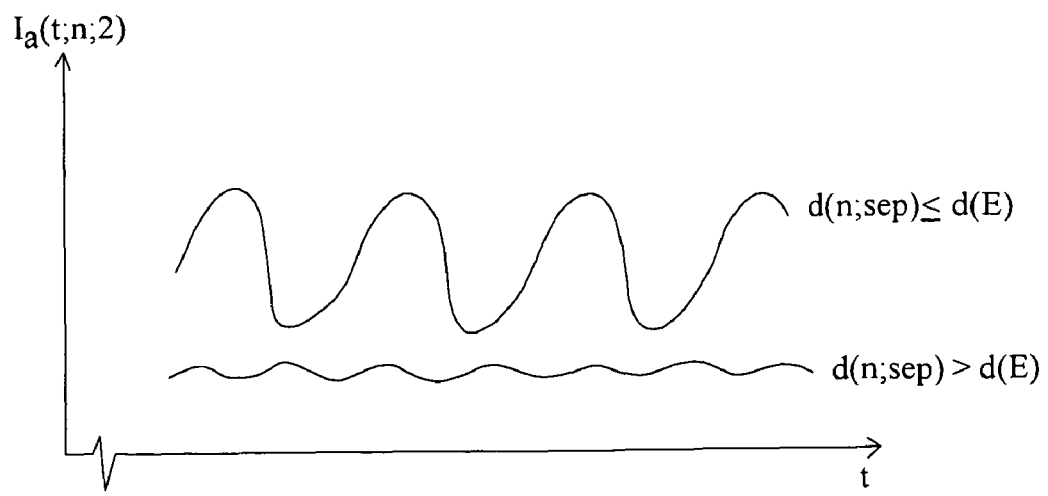

In a second version, where the condition (A-2) is satisfied for a combatant 61-$n$, the system issues a second audible (or visual) warning signal $s_a(t; n; 2)$, which has (i) a rapidly varying, preferably undulatory, frequency $f_i(t; n; var)$ and/or (ii) a rapidly varying, preferably undulatory, signal intensity $I_i(t; n; var)$, as illustrated in FIGS. 9A and 9B, to make the combatant aware of this condition. Where the condition (A-2)

is not satisfied, the system issues a distinguishable audible (or visual) warning signal, for example, a constant frequency and/or constant intensity signal. In the first and second embodiments, the signal intensity of the output signal $s_{i,n}(t)$ is preferably low enough, and/or the angular distribution of the signal intensity is sufficiently narrow, so that this warning signal is audible (or visible) only to an individual combatant 61-*n*.

In a third version, the receiver-processor 63-*n*1 worn or carried by at least one combatant 61-*n*1 does not include an LD system so that this combatant and the associated receiver-processor 63-*n*1 are not aware of the corresponding location coordinates of this combatant. In this situation, it is preferable that at least one reference receiver-processor 63-*n*2 includes an LD system so that the corresponding reference combatant 61-*n*2 and the associated reference receiver-processor 63-*n*2 are aware of the corresponding location coordinates for this reference combatant. The receiver-processor 63-*n*2 receives the TPI signals from the TPI source(s) 66-*p* and determines the separation distance d(n; sep) for itself as in Eq. (A-1). If the condition (A-2) is satisfied, with n=n2, the receiver-processor 63-*n*2 generates the audible (or visual) first warning signal $s_a$(t; n; decr; 1), which is loud or intense enough to be recognized by any combatant within a selected distance D (e.g., D=50-100 meters) from the location of the reference combatant 63-*n*2. As in the first embodiment, the first audible (or visual) warning signal $s_i$(t; n; decr or incr) has a monotonically decreasing frequency, f=$f_fl$(t; n; decr) (FIG. 8A) or a monotone increasing frequency, f=$f_i$(t; n; incr) (FIG. 8B), and this signal is recognized by all combatants within the distance D from the receiver-processor 63-*n*2. The procedure for the remainder of the third embodiment proceeds as in the first embodiment.

In a fourth version, at least one, but less than all, of the receiver-processors 63-*n*2 includes an LD system, and if d(n; sep)≦d(E), the system issues a second audible (or visual) warning signal $s_a$(t; n; 2) with (i) a rapidly varying, preferably undulatory, frequency $f_a$(t; n; var) and/or (ii) a rapidly varying, preferably undulatory, signal intensity $I_i$(t; n; var), as illustrated in FIGS. 9A and 9B. The remainder of the fourth embodiment proceeds as in the second embodiment.

In each of these versions, a receiver-processor 63-*n* provides a first audible (or visual) warning signal $s_a$(t; n; decr or incr; 1) if the condition (A-2) is satisfied and provides a different, distinguishable warning signal if the condition (A-2) is not satisfied. Two or more distinguishable audible (or visual) warning signals, rather than text-based, symbol-based or color-based (visual) signals, are preferably used here, because an aural system is believed to be more flexible, to offer greater discrimination, and to offer greater range, than does a visual system. The launch site LS may be ground-based or may be part of an airborne or mobile vehicle.

The invention can also be used to estimate an impact effect distance, d(E)=d(E; disablement), for disablement of an equipment item, such as a vehicle, a weapon or an observation instrument, that is located in a geographical region adjacent to the impact site, as graphically illustrated in FIG. 7. Alternatively, a visually perceptible or audibly perceptible warning signal may be issued to indicate that a separation distance d(sep) is no greater than an impact effect distance d(E) for (i) death of a combatant, (ii) serious injury to a combatant, or (iii) disablement of part or all of an equipment item, preferably with a perceptibly different signal being used for each of the categories (i), (ii) and (iii). The different impact effect distances for these three categories should be determined experimentally, at least in part.

Appendix B

Trajectory Equations

Consider a projectile, such as an artillery shell, that is launched from a launch site with initially-unknown launch site coordinates ($x_L$, $y_L$, $z_L$), travels through an atmosphere, and is subject only to atmospheric and gravitational (g) forces, as illustrated in FIG. 6. The projectile 62 has a mass of m and an initial launch velocity v0 immediately after launch, both initially unknown. A suitable second order differential equation describing ballistic motion of the projectile after launch from a launch site LS is $$m(d^2r/dt^2) = F_w - kmg, \quad (B-1)$$

where $F_w$ is an estimated wind force vector (assumed constant), dependent upon the shape parameters and other relevant details of the projectile but not directly upon the mass m, and r(t) is location vector of the projectile at time t.

Where the wind force is negligible or is ignored, a suitable solution of Eq. (B-1) is $$r(t) = \{(F_w/m) - kg\}(t-t0)^2/2 + b(t-t0) + c, \quad (B-2)$$

$$b = b(i1, i2) = \{r(t_{i2}) - r(t_{i1})\}/(t_{i2} - t_{i1})\{(F_w/m) - kg\}(t_{i1} + t_{i2} - 2t_0), \quad (B-3)$$

$$c = c(i1, i2) = \{r(t_{i1}) + r(t_{i2}) + \{(F_w/m) - kg\}\{(t_{i2} - t_0)^2\}\}/2, \quad (B-4)$$

where r(t=$t_{i1}$) and r(t=$t_{i2}$) are two observations of location coordinates for the projectile at distinct times t=$t_{i1}$ and t=$t_{i2}$ (I=1, 2, . . . ), and $t_0$ is a selected but arbitrary time value (e.g., $t_0$=($t_{i1}$+$t_{i2}$)/2). Where the observation time values $t_{i1}$ and $t_{i2}$ are known, the solution r(t) can be extended backward and forward in time to estimate a launch time, t=$t_L$, a corresponding launch site LS, an impact time, t=$t_I$, and a corresponding impact site IS for which $$r(t_L) \in S1, \quad (B-5a)$$

$$r(t_I) \in S2, \quad (B-5b)$$

where $S_L$ is a known launch surface and $S_I$ is a known impact surface (e.g., planar or spheroidal). The launch time, t=$t_L$, the impact time, t=$t_I$, the launch site coordinates ($x_L$, $y_L$, $z_L$), and the impact site coordinates ($x_I$, $y_I$, $z_I$), are estimated from Eqs. (B-2), (B-3) and (B-4).

Two or more projectile observations (at times t=$t_{i1}$ and t=$t_{i2}$ with $t_{i1}$<$t_{i2}$) from each of two or more spaced apart observers are used to provide trajectory vector values r($t_{i1}$) and r($t_{i2}$). Where projectile observations are available at J>2 distinct times, t=$t_{ij}$(j=1, . . . , J≧3), with $t_{i1}$<$t_{i2}$<. . . $t_{i,J}$, one can obtain a potentially more accurate estimation of the trajectory by replacing the trajectory parameters b(i1,i2) and c(i1,i2) with filtered or statistically weighted parameter values, b^ and c^, respectively, defined by $$b^\wedge = \sum_{j=1}^{J} \sum_{j'=j+1}^{J} h(ij, ij') b(ij, ij'), \quad (B-6)$$

-continued $$\hat{c} = \sum_{j=1}^{J} \sum_{j'=j+1}^{J} h(ij, ij') c(ij, ij') \qquad (B-7)$$

where h(ij,ij') are normalized, non-negative filter weights satisfying $$h(ij,ij') \geq 0 (j' < j), \qquad (B-8)$$

$$\Sigma h(ij,ij') = 1 \qquad (B-8)$$

$j \leq j'$

The projectile launch velocity $$(dr/dt)_{t=t_L} = v_0 = \{F_w/m - \text{kg}\}(t_L - t0) + b, \qquad (B-10)$$

determined immediately after launch, may be computed and used to estimate the projectile explosive load E, relying in part upon a database of launch velocity $v_0$ for each of the different projectiles in the adversary's arsenal. The projectile explosive load E plus a reference curve or database of separation distance d(E) for serious injury or lethality (FIGS. 8A and 8B) is used to estimate whether a combatant is within a probable injury or lethality region for the estimated impact site.

Where the value of $F_w$ is known (e.g., from local wind observations), the projectile mass m can be estimated. By consulting an appropriate database of the adversary's projectiles and comparing the projectile launch velocity, determined immediately after launch, plus the projectile mass m, an estimate of projectile explosive load E can be made. Using the information contained in FIG. 7 for the particular projectile used, an impact effect distance d(E) corresponding to serious injury or lethality or equipment disablement can be estimated and used in the preceding development in connection with Eq. (A-2) to determine which audible (or visual) warning signal $s_{a,n}(t)$ should be provided for a particular combatant, or for all combatants. in a given region. Two or more different warning signals may be provided, corresponding to different dangers from projectile impact.

Appendix C

Trajectory Observations

Figure 10:
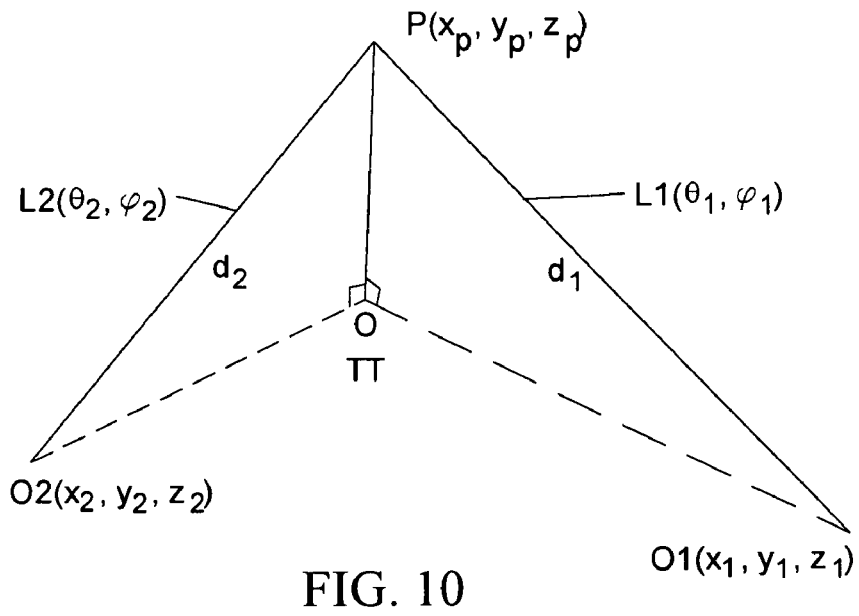
FIG. 10 schematically illustrates determination of present location of a projectile, using observations from two spaced apart observation sites.

FIG. 10 illustrates a projectile that is observed at substantially the same time at each of two (or more) known observation locations, O1 and O2, having the respective location coordinates $(x_1, y_1, z_1)$ and $(x_2, y_2, z_2)$. Each of these observers observes a projectile P with unknown location coordinates $(x_P, y_P, z_P)$ at substantially the same time, through measurements of a separation distance $d_m (m=1, 2)$ and spherical coordinates $(\phi_m, \theta_m)$, measured relative to a line of sight segment $L_m$ from Om to P. The observer locations, O1 and O2 and present projectile location P have coordinates referenced to an arbitrary but fixed coordinate system, including a plane Π determined by line segments O-O1 and O-O2.

A directly measured separation distance $d_m$ can be determined by measuring a round trip return time of a radar or other electromagnetic, electronic or acoustic signal, issued at Om and received as a reflected return signal a time $\Delta t_m$ later, $$d_m(\text{meas}) = c(\Delta t_m)/2 (m=1,2) \qquad (C-1)$$

where c is a velocity of signal propagation in the ambient medium.

The line of sight segment $L_m$ from Om to P is described parametrically as follows for each observation point:

$$x = d \cos \theta_m \cos \phi_m + x_m, \qquad (C-2a)$$

$$y = d \cos \theta_m \sin \phi_m + y_m, \qquad (C-2b)$$

$$z = d \sin \theta_m + z_m, \qquad (C-2c)$$

where $(\theta, \phi)$ are spherical coordinates, referenced to the same coordinate system, and d is the distance along the line of sight $L_m$. From the Eqs. (C-2), one recovers consistency relations, $$(x-x_m)^2 + (y-y_m)^2 + (z-z_m)^2 = d^2 \{\cos^2\theta_m \cos^2\phi_m + \cos^2\theta_m \sin^2\phi_m + \sin^2\theta_m\} = d^2 \qquad (C-3)$$

Equations (C-2a) and (C-2b) can be re-expressed as $$(x-x_m)/\{\cos \theta_m \cos \phi_m\} = (y-y_m)/\{\cos \theta_m \sin \phi_m\} = (z-z_m)/\{\sin \theta_m\} = d_m. \qquad (C-4)$$

The location $(x_P, y_P, z_P)$ is the unique intersection of the line of sight segments $L_1$ and $L_2$. From Eqs. (C-2a) and (C-2b) one infers that $$\begin{vmatrix} d_1 \\ d_2 \end{vmatrix} = \{\det(M)\}^{-1} \begin{vmatrix} -\cos\theta_2\sin\phi_2 & \cos\theta_2\cos\phi_2 \\ -\cos\theta_1\sin\phi_1 & \cos\theta_1\cos\phi_1 \end{vmatrix} \begin{vmatrix} x_2 - x_1 \\ y_2 - y_1 \end{vmatrix}, \qquad (C-5)$$

$$\det(M) = \cos \eta_2 \cos \eta_2 \sin(\phi_1 - \phi_2) \qquad (C-6)$$

$$x_P = x_1 + d_1 \cos \theta_1 \cos \phi_1 = x_2 + d_2 \cos \theta_2 \cos \phi_2, \qquad (C-7)$$

$$y_P = y_1 + d_1 \cos \theta_1 \sin \phi_1 = y_2 + d_2 \cos \theta_2 \sin \phi_2, \qquad (C-8)$$

$$z_P = z_1 + d_1 \sin \theta_1 = z_2 + d_2 \sin \theta_2, \qquad (C-9)$$

from which the present location coordinates $(x_P, y_P, z_P)$ can be estimated.

Figure 11:
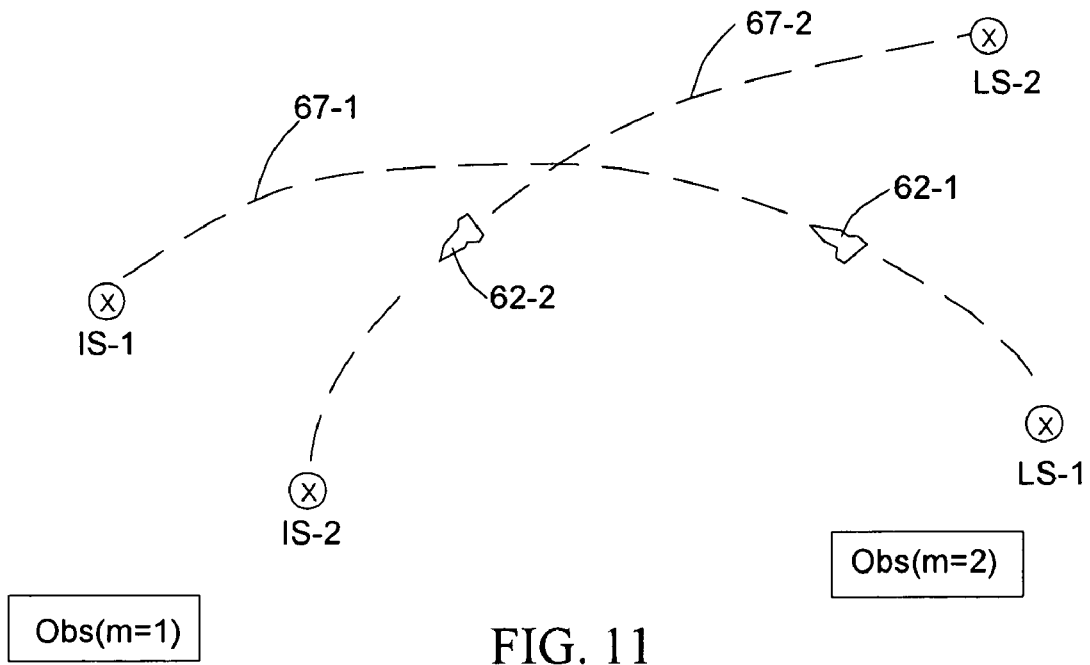
FIG. 11 schematically illustrates distinction between trajectories of two different projectiles.

FIG. 11 illustrates a situation in which two (or more) distinct projectiles, 62-1 and 62-2, following different trajectories, 67-1 and 67-2, are present at the same time so that trajectory confusion is possible. For convenience, it is assumed that two observation sites, numbers m and m', are paired with each other for estimation of the present values of the projectile coordinates $(x_P, y_P, z_P)$ and that transmission of the interrogation signals from each of these two paired sites are coordinated, preferably occurring at substantially the same time.

As a first approach to suppressing the possibility of confusion, each (first) observation site may use a different interrogation frequency f1(interr) and f2(interr), such as a distinguishable radar return frequency, and each observation site (m=1, 2) filters the return signal(s), discussed in the preceding, to identify its own return signal and to determine the observation site-projectile separation distance $d_{OmP}$ for itself. Where the first observation site (m) is also aware of the interrogation frequency $f_{m'}$(interr) used by the second observation site (number m'≠m) to cooperatively determine the present location coordinates $(x_P, y_P, z_P)$ of the projectile, as discussed in the preceding, the elapsed time $\Delta t_{m'}$ and separation distance $d_{Om'P}$ associated with a return signal for the second site can be estimated at the first site as $$\Delta t_{m'}(\text{est}) = \Delta t_m + (t_{m'} - t_m), \qquad (C-10)$$

$$d_{m'}(\text{est}) = c(\Delta t_{m'})/2, \qquad (C-11)$$

where $t_m$ and $t_{m'}$ are the measured absolute times for receipt, at the first site, of the return signals with the associated return frequencies f1(interr) and f2(interr), respectively. The estimated separation distances, $d_m$(est) and the directly measured separation distance $d_m$(meas), for the two paired observation sites can be compared with each other (for m=1 and, separately, for m=2) to confirm or refute the hypothesis that each of the two paired sites is observing the same projectile. If each of the two paired sites is observing a different projectile, at least one of the two pairs of compared separation times, $\Delta t_m$(est) and $\Delta t_m$(meas), should be in substantial disagreement with the other corresponding separation time.

This approach relies upon (1) filtering the return signals received in order to distinguish between the return signal frequencies f1(interr), f2(interr) and any other return signal frequency (2) use of separate return signal gating, at the first site and/or at the second site, of the return signals for the first and second sites.

In a second approach, the projectile coordinates $(x_P, y_P, z_P)_{t=ti}$ are determined from observations at times $t=t_i$ (i=1, 2, 3, 4) with $t_1 < t_2 \ll t_3 < t_4$. The projectile trajectory parameters for $t_i=t_1$ and $t=t_2$ are compared with the corresponding projectile trajectory parameters for $t_i=t_3$ and $t=t_4$. If the corresponding parameters are sufficiently close to each other, this tends to confirm the hypothesis that each of the two paired sites is observing the same projectile. If the two sets of corresponding trajectory parameters are markedly different from each other, this indicates that each of the first and second observation sites is likely observing a different projectile.

What is claimed is:

1. A method for enhancing or extending a vision system of a human being, the method comprising providing a computer that is programmed:
   to represent at least one selected visual image region, having at least one color or hue associated with the region, in terms of at least one visual image parameter for the region, the at least one visual image parameter including at least one of: vertical coordinate range of the region; horizontal coordinate range of the region; center coordinates for the region; region brightness; dominant hue range or wavelength range of the region; change in a parameter value that characterizes the visual image, with respect to a reference parameter value; and time rate of change TRC in a parameter value that helps characterize the visual image region;
   to associate each of the visual image parameters with at least one of a first set of M1 audio signal attributes (M1≧1), the first set of attributes being drawn from signal carrier frequency, signal envelope frequency, carrier signal-envelope signal phase difference at a selected time, baseline amplitude, envelope signal amplitude relative to baseline amplitude, and signal time duration, and with a second set of at least one of M2 audio signal attributes (M2≧1), the second set of attributes being drawn from time rate of change of envelope frequency and time-rate-of-change of baseline amplitude;
   to allow the selected visual image region to be adjusted in at least one of a horizontal dimension and a vertical dimension so that the visual image region primarily includes a selected object whose apparent diameter is increasing with time or is decreasing with time; and
   to present the M1+M2 audio signal attributes sequentially or simultaneously for the at least one selected region.

2. The method of claim 1, wherein said computer is further programmed to provide a presentation format in which at least one of said signal carrier frequency, said signal envelope frequency, said signal carrier-signal envelope phase difference, said baseline amplitude, said time-rate-of-change of said baseline amplitude, said envelope signal amplitude relative to said baseline amplitude, and said signal time duration changes monotonically with at least one of a coordinate representing said vertical location of said visual image region, a coordinate representing said horizontal location of said corresponding visual image region, one or more coordinates representing a range of horizontal coordinates of said corresponding visual image region, one or more coordinates representing a range of vertical coordinates of said corresponding visual image region, a coordinate representing brightness of said corresponding visual image component, and a coordinate representing said dominant wavelength or dominant hue of said corresponding visual image region.

3. The method of claim 2, wherein said computer is further programmed to choose said monotonic change to be at least one of (a) a logarithmic change, (b) a power law change and (c) a linear change.

4. The method of claim 2, wherein said computer is further programmed to choose said monotonic change to be a monotonically increasing change.

5. The method of claim 2, wherein said computer is further programmed to choose said monotonic change to be a monotonically decreasing change.

6. The method of claim 1, wherein said computer is further programmed:
   to determine said dominant hue or wavelength by a process comprising determining at least one selected wavelength range, drawn from wavelength ranges in ultraviolet, visible, near infrared and mid-infrared wavelengths, that contains said dominant hue or wavelength for said visual image component; and
   to associate said at least one of said audio signal attributes with the selected wavelength range.

7. The method of claim 1, further comprising providing said at least one of said four audio signal attributes for a selected recipient whose sight is impaired.

8. The method of claim 1, further comprising providing at least one of said signal carrier frequency and said signal envelope frequency in a frequency range determined by hearing acuity of a selected recipient.

9. The method of claim 1, further comprising choosing said at least one visual image component to have at least one selected wavelength that is part of at least one of an ultraviolet spectrum, a near-infrared spectrum and a mid-infrared spectrum.

10. The method of claim 1, further comprising representing, to a selected recipient having an auditory communication system, said at least one of said audio signal attributes with at least one frequency to which the selected recipient's auditory communication system is sensitive.

11. The method of claim 1, further comprising providing said visual image component for said region that cannot be accurately perceived visually because of at least one of signal interference, signal distortion and signal attenuation by an ambient environment.

12. The method of claim 11, wherein said ambient environment includes at least one of rain, snow, ice, hail, sleet, fog, condensation, lightning, and transition between daylight and nighttime.

13. The method of claim 1, further comprising choosing said at least one of said audio signal attributes so that said at least one audio signal attribute can be transmitted through an environment with at least one of reduced signal interference, reduced signal distortion and reduced signal attenuation.

14. The method of claim 1, further comprising analyzing said change in said parameter that characterizes said visual image.

15. The method of claim 1, further comprising:
identifying at least one of said time rate of change TRC of said parameter value that helps characterize said region; and
representing said time rate of change TRC of said parameter value as at least one of: (i) a continuous change with time, (ii) a discrete change at two or more spaced apart times, and (iii) a discrete change, only when a magnitude of a difference between a first value of said parameter and a second value of said parameter is at least equal to a selected threshold magnitude.

16. A system for enhancing or extending a vision system of a human being, the system comprising providing a computer that is programmed:
to represent at least one selected visual image region, having at least one color or hue associated with the region, in terms of at least one visual image parameter for the region, the at least one visual image parameter including at least one of: vertical coordinate range of the region; horizontal coordinate range of the region; center coordinates for the region; region brightness; dominant hue range or wavelength range of the region; change in a parameter value that characterizes the visual image, with respect to a reference parameter value; and time rate of change TRC in a parameter value that helps characterize the visual image region;
to associate each of the visual image parameters with at least one of a first set of M1 audio signal attributes (M1≧1), the first set of attributes being drawn from signal carrier frequency, signal envelope frequency, carrier signal-envelope signal phase difference at a selected time, baseline amplitude, envelope signal amplitude relative to baseline amplitude, and signal time duration, and with a second set of at least one of M2 audio signal attributes (M2≧1), the second set of attributes being drawn from time rate of change of envelope frequency and time-rate-of-change of baseline amplitude; and
to analyze an object, within the visual image region, that is moving toward a viewer or away from a viewer of the visual image region so that a lateral diameter of the object is increasing or is decreasing, respectively, and to transmit at least one of said M1+M2 audio signal attributes so that at least one of a signal frequency and a signal amplitude is increasing or decreasing in time at a rate corresponding to the increase or decrease in the lateral diameter with time; and
to present the M1+M2 audio signal attributes sequentially or simultaneously for the at least one selected region.

17. The system of claim 16, wherein said computer is further programmed to provide a presentation format in which at least one of said signal carrier frequency, said signal envelope frequency, said signal carrier-signal envelope phase difference, said baseline amplitude, said time-rate-of-change of said baseline amplitude, said envelope signal amplitude relative to said baseline amplitude, and said signal time duration changes monotonically with at least one of a coordinate representing said vertical location of said visual image region, a coordinate representing said horizontal location of said corresponding visual image region, one or more coordinates representing a range of horizontal coordinates of said corresponding visual image region, one or more coordinates representing a range of vertical coordinates of said corresponding visual image region, a coordinate representing brightness of said corresponding visual image component, and a coordinate representing said dominant wavelength or dominant hue of said corresponding visual image region.

18. The system of claim 17, wherein said computer is further programmed to choose said monotonic change to be at least one of (a) a logarithmic change, (b) a power law change and (c) a linear change.

19. The system of claim 17, wherein said computer is further programmed to choose said monotonic change to be a monotonically increasing change.

20. The system of claim 17, wherein said computer is further programmed to choose said monotonic change to be a monotonically decreasing change.

21. The system of claim 16, wherein said computer is further programmed:
to determine said dominant hue or wavelength by a process comprising determining at least one selected wavelength range, drawn from wavelength ranges in ultraviolet, visible, near infrared and mid-infrared wavelengths, that contains said dominant hue or wavelength for said visual image component; and
to associate said at least one of said audio signal attributes with the selected wavelength range.

22. The system of claim 16, wherein said at least one of said four audio signal attributes is provided for a selected recipient whose sight is impaired.

23. The system of claim 16, wherein at least one of said signal carrier frequency and said signal envelope frequency is provided in a frequency range determined by hearing acuity of a selected recipient.

24. The system of claim 16, wherein said at least one visual image component has at least one selected wavelength that is part of at least one of an ultraviolet spectrum, a near-infrared spectrum and a mid-infrared spectrum.

25. The system of claim 16, further comprising an auditory communication system that represents, to a selected recipient, said at least one of said audio signal attributes with at least one frequency to which the selected recipient's auditory communication system is sensitive.

26. The system of claim 16, wherein said visual image component for said region cannot be accurately perceived visually because of at least one of signal interference, signal distortion and signal attenuation by an ambient environment.

27. The system of claim 26, wherein said ambient environment includes at least one of rain, snow, ice, hail, sleet, fog, condensation, lightning, and transition between daylight and nighttime.

28. The system of claim 16, wherein said at least one of said audio signal attributes is chosen so that said at least one audio signal attribute can be transmitted through an environment with at least one of reduced signal interference, reduced signal distortion and reduced signal attenuation.

29. The system of claim 16, wherein said computer is further programmed to analyze said change in said parameter that characterizes said visual image.

30. The system of claim 16, wherein said computer is further programmed:
to identify at least one of said time rate of change TRC of said parameter value that helps characterize said region; and
to represent said time rate of change TRC of said parameter value as at least one of: (i) a continuous change with time, (ii) a discrete change at two or more spaced apart times, and (iii) a discrete change, only when a magnitude of a difference between a first value of said parameter and a second value of said parameter is at least equal to a selected threshold magnitude.

31. A method for enhancing or extending a vision system of a human being, the method comprising providing a computer that is programmed:

to represent at least one selected visual image region, having at least one color or hue associated with the region, in terms of at least one visual image parameter for the region, the at least one visual image parameter including at least one of: vertical coordinate range of the region; horizontal coordinate range of the region; center coordinates for the region; region brightness; dominant hue range or wavelength range of the region; change in a parameter value that characterizes the visual image, with respect to a reference parameter value; and time rate of change TRC in a parameter value that helps characterize the visual image region;

to associate each of the visual image parameters with at least one of a first set of M1 audio signal attributes (M1≧1), the first set of attributes being drawn from signal carrier frequency, signal envelope frequency, carrier signal-envelope signal phase difference at a selected time, baseline amplitude, envelope signal amplitude relative to baseline amplitude, and signal time duration, and with a second set of at least one of M2 audio signal attributes (M2≧1), the second set of attributes being drawn from time rate of change of envelope frequency and time-rate-of-change of baseline amplitude;

to analyze an object, within the visual image region, that is moving toward a viewer or away from a viewer of the visual image region so that a lateral diameter of the object is increasing or is decreasing, respectively, and to transmit at least one of said M1+M2 audio signal attributes so that at least one of a signal frequency and a signal amplitude is increasing or decreasing in time at a rate corresponding to the increase or decrease in the lateral diameter with time; and to present the M1+M2 audio signal attributes sequentially or simultaneously for the at least one selected region.

32. A system for enhancing or extending a vision system of a human being, the system comprising providing a computer that is programmed:

to represent at least one selected visual image region, having at least one color or hue associated with the region, in terms of at least one visual image parameter for the region, the at least one visual image parameter including at least one of: vertical coordinate range of the region; horizontal coordinate range of the region; center coordinates for the region; region brightness; dominant hue range or wavelength range of the region; change in a parameter value that characterizes the visual image, with respect to a reference parameter value; and time rate of change TRC in a parameter value that helps characterize the visual image region;

to associate each of the visual image parameters with at least one of a first set of M1 audio signal attributes (M1≧1), the first set of attributes being drawn from signal carrier frequency, signal envelope frequency, carrier signal-envelope signal phase difference at a selected time, baseline amplitude, envelope signal amplitude relative to baseline amplitude, and signal time duration, and with a second set of at least one of M2 audio signal attributes (M2≧1), the second set of attributes being drawn from time rate of change of envelope frequency and time-rate-of-change of baseline amplitude;

to allow the selected visual image region to be reduced in at least one of a horizontal dimension and a vertical dimension so that the visual image region primarily includes a selected object whose apparent diameter is increasing with time or is decreasing with time; and to present the M1+M2 audio signal attributes sequentially or simultaneously for the at least one selected region.

33. A method for enhancing or extending a vision system of a human being, the method comprising providing a computer that is programmed:

to represent at least one selected visual image region, having at least one color or hue associated with the region, in terms of at least one visual image parameter for the region, the at least one visual image parameter including at least one of: vertical coordinate range of the region; horizontal coordinate range, of the region; center coordinates for the region; region brightness; dominant hue range or wavelength range of the region; change in a parameter value that characterizes the visual image, with respect to a reference parameter value; and time rate of change TRC in a parameter value that helps characterize the visual image region;

to associate each of the visual image parameters with at least one of a first set of M1 audio signal attributes (M1≧1), the first set of attributes being drawn from signal carrier frequency, signal envelope frequency, carrier signal-envelope signal phase difference at a selected time, baseline amplitude, envelope signal amplitude relative to baseline amplitude, and signal time duration, and with a second set of at least one of M2 audio signal attributes (M2≧1), the second set of attributes being drawn from time rate of change of envelope frequency and time-rate-of-change of baseline amplitude;

to present the M1+M2 audio signal attributes sequentially or simultaneously for the at least one selected region as an audibly perceptible signal (APS) that is representable as an equation $$S_a(t) = b(t) + a(t)\sin\{f_e(t)t + \Phi_e\}\sin\{f_c t + \Phi_c\}$$

where b(t) is a baseline amplitude for the APS, expressed as a function of time t and having a time rate of change db/dt associated with the baseline amplitude, a(t) is an envelope signal amplitude, $f_e(t)$ is a signal envelope frequency, which may vary with the time t, $\phi_e$ is a signal envelope phase, $f_c$ is a carrier signal frequency, and $\Phi_c$ a carrier signal phase; and to analyze an object, within the visual image region, that is moving toward a viewer or away from a viewer of the visual image region so that a lateral diameter of the object is increasing or is decreasing, respectively, and to transmit at least one of said M1+M2 audio signal attributes so that at least one of a signal frequency, $f_c(t)$ or $f_c$, and a signal amplitude, a(t) or b(t), is increasing or decreasing in time at a rate corresponding to the increase or decrease in diameter with time.

* * * * *